United States Patent [19]

Cohen

[11] Patent Number: 4,597,960
[45] Date of Patent: Jul. 1, 1986

[54] MICROENCAPSULATED ASTRINGENT HEMOSTATIC AGENTS AND METHODS OF USE

[76] Inventor: Edgar C. Cohen, 4123 Vincennes Pl., New Orleans, La. 70125

[21] Appl. No.: 500,689

[22] Filed: Jun. 3, 1983

Related U.S. Application Data

[63] Continuation-in-part of Ser. No. 486,472, Apr. 19, 1983, abandoned.

[51] Int. Cl.$^4$ .................. A61K 33/06; A61K 33/26; A01N 59/06; A01N 59/16
[52] U.S. Cl. ..................................... 424/28; 424/35; 424/147; 424/154
[58] Field of Search ................. 424/28, 35, 147, 330, 424/154

[56] References Cited

U.S. PATENT DOCUMENTS

| | | | |
|---|---|---|---|
| 2,371,862 | 3/1945 | Wershaw | 424/154 |
| 3,238,620 | 3/1966 | Robertson . | |
| 3,538,214 | 11/1970 | Polli et al. | 424/35 |
| 3,873,588 | 3/1975 | Osawa et al. | 526/241 |
| 4,102,806 | 7/1978 | Kondo et al. | 252/316 |
| 4,146,605 | 3/1979 | Ritchey | 424/154 |
| 4,166,108 | 8/1979 | Brown et al. | 424/28 |
| 4,260,597 | 4/1981 | Porteous | 424/49 |
| 4,268,496 | 5/1981 | Ohno et al. | 424/35 |
| 4,276,287 | 6/1981 | Cabardo, Jr. | 424/154 |
| 4,329,333 | 5/1982 | Barr | 424/19 |
| 4,395,398 | 6/1983 | Yamamoto | 424/147 |
| 4,486,412 | 12/1984 | Shaw et al. | 424/154 |

Primary Examiner—Morton Foelak
Assistant Examiner—Kriellion Morgan
Attorney, Agent, or Firm—Griffin, Branigan, & Butler

[57] ABSTRACT

An astringent hemostatic composition comprised of a micron-sized astringent hemostatic agent microencapsulated in a biocompatible and non-allergenic hemostatic polymer soluble in body fluids. The composition may be used intraorally or dermatologically. For intraoral purposes, the preferred composition is ferric sulfate microencapsulated in ethyl cellulose material. The composition of the invention may be used in a method for effecting gingival retraction. In the method, the microencapsulated astringent hemostatic composition is introduced into the gingival sulcus and is compacted by the patient biting onto bite registration material. A plurality of different microencapsulated astringent hemostatic agents having different time-release properties may be assembled in a kit form allowing a practitioner to formulate a specific formulation designed to treat a specific injury or condition.

An astringent hemostatic composition of the invention may be used in a bandage for covering a wound. In one bandage embodiment, the gauze or sponge pad is sprayed with a biocompatible adhesive onto which a dusting of astringent hemostatic composition of the invention is applied. In a second bandage embodiment, a layer or dusting of astringent hemostatic composition of the invention is sandwiched between an upper and lower gauze or sponge layer. In a third bandage embodiment, an astringent hemostatic composition of the invention is adhered to a transdermal bandage using a biocompatible adhesive.

12 Claims, 2 Drawing Figures

4,597,960

MICROENCAPSULATED ASTRINGENT HEMOSTATIC AGENTS AND METHODS OF USE

This is a continuation-in-part of Ser. No. 486,472, filed Apr. 19, 1983, now abandoned.

BACKGROUND OF THE INVENTION

This invention relates to hemostatic therapeutic compositions and, more particularly to compositions and methods for bringing about hemostasis intraorally or for dermatological applications.

In dentistry, it is often required to temporarily retract gingival tissues in order to prepare patients for taking impressions, setting crowns, or providing other dental therapeutic treatment. Presently, an often used method for bringing about gingival retraction is a mechanical method involving insertion of a gingival retraction cord into the sulcus between the gingiva and the tooth. This method poses several problems. Gingival retraction cords often produce excessive mechanical retraction which is often irreversible. Also, many cords deteriorate following subgingival placement and are difficult to retrieve. Remnants of cord fibers are often entrapped in the sulcus, and this condition usually elicits a foreign body reaction and may result in distorted impressions.

Another present method for retracting gingival tissue involves the direction application of an astringent solution to the gingival crevice. A problem associated with the use of present astringent solutions is that they generally rapidly flow away from the gingival crevice and do not sustain their astringent action for an adequate period of time.

An additional requirement in a procedure for bringing about gingival retraction is maintaining hemostasis. Use of a gingival retraction cord as described above is a cause of substantial capillary hemorrhage. Use of readily washed away astringent solutions is often ineffective for bringing about adequate hemostasis.

For both intraoral and dermatological applications, present astringent and hemostatic materials for application to body tissues are comprised of active ingredients which immediately react with the body tissues upon contact therewith. If a practitioner applies an excessively large quantity of such material to the tissues, then those tissues are immediately subjected to an excessively large quantity of reactive agent. A problem that may result from such an occurrence is that delicate tissues may be irritated by the excess astringent substances.

Presently used gingival retraction agents are most commonly aluminum base materials. This is so because the aluminum base materials are readily impregnated into conventional gingival retraction cord material. Even though it is known that ferric sulfate astringent is milder and less iritating to gingival tissues, ferric sulfate is not generally used as an impregnant for gingival cords because of its inferior ability to impregnate into the cord.

The present art of bandages to be applied topically to skin surfaces discloses astringent hemostatic agents impregnated into bandage substrate materials. However, there are problems associated with such bandages which are similar to problems associated with conventionally impregnated gingival retraction cords relating to an excess of astringent agent being applied to delicate body tissues. There are no bandages presently impregnated with astringent agents that are released only upon demand.

Accordingly, it is an object of the invention to provide an astringent and hemostatic composition which provides an active astringent and hemostatic agent on demand for contact with body tissues and therefore does not subject the delicate tissues to excessive quantities of reactive agents which cause tissue irritation.

An advantage of the invention is the provision of a composition and method for bringing about reversible gingival retraction and effective hemostasis.

Another advantage of the invention is the provision of a method which does not rely upon mechanical structures such as a cord for bringing about gingival retraction.

Still another advantage of the invention is the provision of an astringent composition which brings about gingival retraction and provides hemostasis without readily washing away.

Yet another advantage of the invention is the provision of a method and composition for controlling the amount of active hemostatic agent which contacts the gingival tissues.

Another advantage of the invention is the provision of a composition and method for applying ferric sulfate astringent in adequate quantities to gingival tissues.

Another advantage of the invention is the provision of a bandage for topical application to skin areas wherein the bandage contains an astringent hemostatic agent which is released on demand.

SUMMARY OF THE INVENTION

In accordance with one aspect of this invention, a novel composition is provided for producing capillary hemostasis. The composition of the invention may be used intraorally or for dermatological applications. The composition is comprised of a powdered astringent hemostatic agent microencapsulated with a polymer that has hemostatic properties, is biologically inert; is compatible with human tissue; and, is non-allergenic.

When used intraorally the composition of the invention may be used to bring about both gingival retraction and hemostasis. For intraoral applications the preferred microencapsulated astringent hemostatic agent is ferric sulfate and the preferred encapsulation material is ethyl cellulose. Other microencapsulated astringents may be selected from the group consisting of aluminum sulfate, aluminum chloride, and the like.

The microencapsulated astringent hemostatic agent may also be used in conjunction with microencapsulated epinephrine granules.

The microencapsulated astringent hemostatic agent of the invention serves to release the active agent from the microcapsule in a time-release manner. A variety of different particle size astringent hemostatic agents may be encapsulated in capsules having a variety of capsule wall thickness. Thereby, release of active agent from microcapsules may be sustained at a controlled rate over an extended period of time.

In accordance with another aspect of the invention, a method is provided for bringing about gingival retraction and hemostasis wherein the time-released astringent hemostatic agent of the invention is introduced into the gingival sulcus. When the time-released astringents are inside the gingival sulcus, the active astringent reagent contacts the gingival tissue only when the time-release encapsulation material dissolves and the inner reagent is released. Thus, the time-release astringent act solely on a demand basis; that is, the greater the amount of capillary hemorrhage or bleeding the more astringent reagent is released and directly contacts the gingival tissue to produce clotting and capillary closure.

The mass of time-release astringent hemostatic agent introduced into the gingival sulcus is compacted within the sulcus and acts as a gentle, atraumatic, and non-structural mechanical gingival retraction means. The compaction of time-released gingival retraction within the gingival sulcus may be brought about by compaction with a hand instrument.

Once the time-release astringent hemostatic composition of the invention is introduced into the gingival sulcus, the composition may be distributed about the base of the tooth within the sulcus by having the patient bite into a quantity of bite registration material. As a result of biting upon the bite registration material, the time-release astringent composition is compacted into the sulcus and gingival retraction is facilitated. The bite registration material serves an additional purpose, that of absorber for excess astringent composition which might otherwise enter the oral cavity as the astringent composition is squeezed out beyond the borders of the gingival sulcus.

In accordance with another aspect of the invention, a bandage for topical application to skin areas is provided having an astringent hemostatic composition of the invention incorporated therein. The astringent hemostatic composition of the invention may be adhesively applied to a conventional gauze or sponge bandage. Alternatively a gauze or sponge sandwich contains a layer of astringent hemostatic composition of the invention situated between an upper and lower absorbent layer.

BRIEF DESCRIPTION OF THE DRAWINGS

The foregoing and other objects, features, and advantages of the invention will be apparent from the following more specific description of preferred embodiments of the invention, as illustrated in the accompanying drawings in which reference characters refer to the same parts throughout the different views. The drawings are not necessarily to scale, emphasis instead being placed upon illustrating principles of the invention in a clear manner.

DETAILED DESCRIPTION OF THE INVENTION

Figure 1:
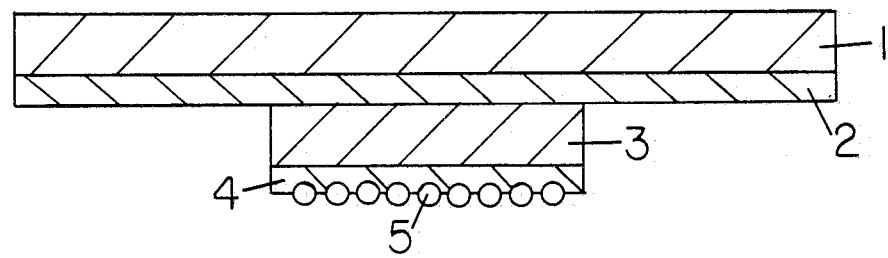
FIG. 1 is a cross-sectional view of one embodiment of the invention.

The preferred composition of the invention for intraoral use which brings about gingival retraction and produces capillary hemostasis is comprised of micromesh ferric sulfate granules encapsulated with a biologically inert and non-allergenic hemostatic polymer such as ethyl cellulose.

Conventional techniques for preparing ferric sulfate particles microencapsulated with a biologically compatible polymer are well known in the art. Teachings of microencapsulation techniques are provided in "Microencapsulation" by Herbig in the Encyclopedia of Chemical Technology, 2nd Edition, Volume 13, published by Kirk-Othmer.

Other astringent materials that may be microencapsulated in accordance with the invention include aluminum sulfate, aluminum chloride and the like.

The preferred encapsulation material, ethyl cellulose, is biologically inert; is compatible with human tissue; is non-allergenic; has hemostatic properties; and is resorbable, Ethyl cellulose is soluble in liquids present in the mouth such as blood and saliva. Ethyl cellulose contributes to blood clotting by acting as a situs for clot formation. The ethyl cellulose can be either water soluble and hydrophobic or water soluble and hydrophilic. Preferably, the ethyl cellulose is water insoluble and hydrophobic.

In addition to intraoral applications of the novel composition of the invention, it has been discovered that the novel compositions of the invention have applicability for hemostasis for dermatological purposes. Astringent hemostatic compositions of the invention suitable for dermatological purposes include microencapsulated ferric sulfate as above and include additionally other microencapsulated astringent hemostatic materials. For example, microencapsulated aluminum sulfate and microencapsulated aluminum chloride are suitable astringent hemostatic agents of the invention for dermatological purposes.

In addition to ethyl cellulose, other cellulose-based polymeric materials soluble in body fluids may serve as coatings for encapsulation of the selected astringent hemostatic agent. Ethyl cellulose is an ethyl ether of cellulose. Other related ethers such as methyl cellulose may also be used for encapsulation of the astringent hemostatic agent to produce a compositioon having time-release properties. Other cellulose ethers have inherent hemostatic properties similar to ethyl cellulose.

In general, oxidized cellulose is a useful class of hemostatic materials. Generally, hemostatic oxidized cellulose materials are also absorbed by body fluids as when used to pack wounds. Some commercial absorbable hemostatic cellulose materials are sold under the names of Oxycel and Hemo-Pak.

It has ben discovered further that epinhphrine may be microencapsulated separately from the astringent, and a blend of microencapsulated epinephrine and microencapsulated astringent hemostatic agent may be formulated. The composite formulation may be used as the astringent hemostatic agent of the invention.

The preferred blend of epinephrine-based material and astringent-based material is 8% microencapsulated epinephrine and 92% microencapsulated astringent (ferric sulfate, aluminum chloride, or aluminum sulfate).

Another satisfactory astringent hemostatic composition of the invention is obtained by blending encapsulated ferric sulfate particles with encapsulated aluminum chloride particles to result in a formulation having approximately 85% encapsulated ferric sulfate particles and 15% encapsulated aluminum chloride particles.

Another suitable astringent hemostatic composition of the inventioon is a blend of the following components in their noted percentages: encapsulated ferric sulfate, 78%; encapsulated aluminum chloride, 14%; and, encapsulated epinephrine, 8%.

In another aspect of the invention, it is possible to suspend an astringent hemostatic composition of the invention in a liquid carrier which does not dissolve the encapsulation material. For example, in one liquid embodiment, 25 grams of encapsulated aluminum chloride and 10 grams of Oxyquinol sulfate are mixed and diluted with non-dissolving liquid carrier to 100 ml.

In another liquid embodiment of the astringent hemostatic composition of the invention, 15 parts encapsulated aluminum chloride or encapsulated aluminum sulfate are mixed with 85 parts of encapsulated ferric sulfate and brought to 100 ml using a non-dissolving liquid carrier.

Although a wide variety of sizes of astringent hemostatic particles and polymer coating thicknesses of encapsulation material may be used, satisfactory compositions of the invention have been obtained by encapsulating micron-mesh astringent with a 3%–6% solution of ethyl cellulose.

In accordance with another aspect of the invention, a method is provided for retracting gingiva and providing hemostasis whereby a quantity of a microencapsulated astringent hemostatic composition of the invention is introduced into the gingival sulcus and compacted into the sulcus by having the patient bite down on bite registration material. The bite registration material may be synthetic such as silicon based or natural such as wax. The bite registration material serves to compact the gingival retractant composition and serves the additional purpose of soaking up excess composition of the invention which exudes out of the sulcus when compression of the material in the sulcus is underway.

In another use of the compositions of the invention, the microencapsulated astringent hemostatic agents can be used in conjunction with gingival retraction cord to further enhance retraction and hemostasis. This can be accomplished in two ways: either the microencapsulated astringent hemostatic agent is applied immediately superior to the subgingivally-placed retraction cord after placement in the sulcus, or microencapsulated astringents are contacted with the surface of a previously dampened gingival retraction cord prior to placement of the cord into subgingival areas.

FIG. 1 shows one bandage embodiment of the invention in cross-section. A conventional bandage may have an outer plastic strip 1 having adhesive coating 2 for adherence to skin surfaces and for retaining a pad of gauze or sponge or other absorbent material 3 which is placed diectly over a wound. In accordance with one bandage embodiment of the invention, a biocompatible second adhesive layer 4 is applied to the surface of gauze or sponge absorbent material 3. Astringent hemostatic composition particles of the invention 5 are sprayed, dusted, or otherwise applied to the adhesive layer 4 on the absorbent material 3. In this way, the astringent hemostatic composition 5 of the invention contacts the wound directly and is released on demand upon contact with wound liquids.

Figure 2:
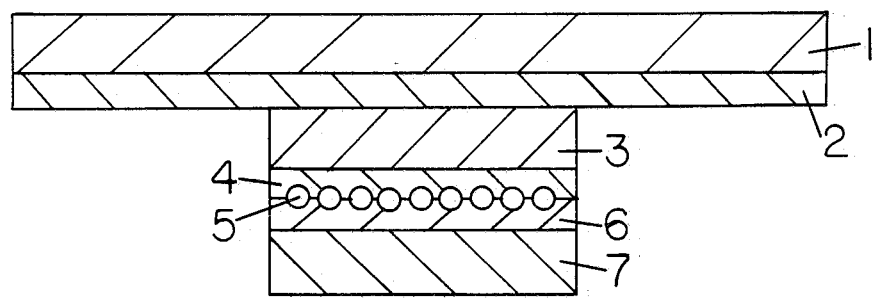
FIG. 2 is a cross-sectional view of a bandage embodiment of the invention wherein the composition of the invention is situated between an upper and lower absorbent layer.

In FIG. 2, a second gauze or sponge absorbent layer 7 having a biocompatible third adhesive layer 6 is applied to the embodiment already described in reference to FIG. 1 above. The additional absorbent layer 7 provides that the astringent hemostatic composition layer 5 of the invention is sandwiched between absorbent materials 3 and 7.

In another bandage embodiment of the invention, a conventional transdermal bandage having a fibrin layer for directly contacting a wound is coated with a powdering of astringent hemostatic agent of the invention.

A plurality of powdered microencapsulated astringent hemostatic agents of the invention may be assembled in a kit form along with other materials such as microencapsulated epinephrine so that a practitioner may customize a particular preparation for particular circumstances that may be confronted. For example, if a skin wound were a relatively shallow abrasion over a relatively large skin surface, the practitioner may formulate a composition of the invention having relatively small amounts of the astringent hemostatic agent because of the relatively small amounts of blood flow. On the other hand, if the skin wound was a deep laceration or tear, a more highly concentrated formulation may be compounded by the practitioner to treat the more localized blood flow of a relatively high rate. In both cases, in accordance with the invention, the release of the microencapsulated astringents hemostatic agent froom the microcapsules is upon demand depending upon contact with body liquids such as blood.

The kit may also include a variety of time-release powder compositions of the invention for any given astringent hemostatic agent so that the practitioner may formulate a particular formulation having time-release properties as may be desired. If the use of the composition of the invention is merely for a short period of time such as for first aid purposes, the practitioner may desire a rapidly released composition of the invention. However, if the applied material is expected to be in use for a considerable length of time, then a formulation having longer time release properties may be employed.

Choice of an actual formulation made from the components in the kit may depend upon additional factors such as age of patient, oiliness or dryness of the patient's skin, the patient's sensitivity to the astringent materials, and other factors.

The embodiments of the invention set forth above are only representative of broad aspects of the invention, and the invention is not to be deemed limited to the particular embodiments set forth. The scope of the invention is to be defined by the claims appended below.

The embodiments of the invention in which an exclusive property or privilege is claimed are defined by the following:

1. A granular composition for producing capillary hemostasis, comprising:
   a granular astringent hemostatic agent selected from the group consisting of ferric and aluminum inorganic salts encapsulated with a cellulose-based biocompatible polymer soluble in body fluids.

2. A composition as described in claim 1 wherein said astringent hemostatic agent is selected from the group consisting of ferric sulfate, aluminum sulfate, and aluminum chloride.

3. A composition as described in claim 1 further including encapsulated epinephrine granules.

4. A kit comprising a plurality of encapsulated astringent hemostatic compositions as described in claim 1 for enabling a practitioner to make a formulation having particular astringent and/or hemostatic properties for a particular treatment.

5. A kit as described in claim 4 wherein, for a specific astringent hemostatic agent, a plurality of encapsulated astringent hemostatic compositions are provided, each having different time-release properties.

6. A composition for producing capillary hemostasis comprised of a blend in the proportions as follows:
   particles of astringent hemostatic agent selected from the group consisting of ferric sulfate, aluminum sulfate, and aluminum chloride encapsulated with cellulose-based materials selected from the group consisting of ethyl cellulose, methyl cellulose, oxycellulose, and oxidized cellulose 82–100% and;
   particles of epinephrine encapsulated with cellulose-base materials selected from the group consisting of ethyl cellulose, methyl cellulose, oxycellulose, and oxidized cellulose 0–18%.

7. A composition for producing capillary hemostasis comprised of a blend in the percentages as follows:
particles of astringent hemostatic agent selected from the group consisting of ferric sulfate, aluminum sulfate, and aluminum chloride encapsulated with cellulose-based materials selected from the group consisting of ethyl cellulose, methyl cellulose, oxycellulose, and oxidized cellulose about 92% and,
particles of epinephrine encapsulated with cellulose-based materials selected from the group consisting of ethyl cellulose, methyl cellulose, oxycellulose, and oxidized cellulose remainder 8%.

8. A composition for producing capillary hemostasis, comprising:
particles of astringent hemostatic agents selected from the group consisting of ferric sulfate, aluminum sulfate, and aluminum chloride encapsulated with cellulose-base materials selected fom the group consisting of ethyl cellulose, methyl cellulose, oxycellulose and oxidized cellulose;
said particles suspended in a liquid carrier which does not dissolve said encapsulation material.

9. A composition for producing capillary hemostasis, comprising:
a granular astringent hemostatic agent selected from the group consisting of ferric and aluminum inorganic salts encapsulated with a cellulose-based biocompatible hemostatic polymer soluble in body fluids.

10. A granular composition for producing capillary hemostasis, comprising:
a granular hemostatic agent selected from the group consisting of ferric and aluminum inorganic salts encapsulated with ethyl cellulose having hemostatic properties.

11. A granular composition for producing capillary hemostasis, comprising:
a granular astringent hemostatic agent selected from the group consisting of ferric and aluminum inorganic salts encapsulated with a cellulose-based biocompatible polymer absorbable in body fluids.

12. A composition for producing capillary hemostasis, comprising:
a granular astringent hemostatic agent selected from the group consisting of ferric and aluminum inorganic salts encapsulated with a cellulose-based biocompatible hemostatic polymer absorbable in body fluids.

* * * * *